US008391964B2

(12) United States Patent
Musley et al.

(10) Patent No.: US 8,391,964 B2
(45) Date of Patent: Mar. 5, 2013

(54) DETECTING ELECTRICAL CONDUCTION ABNORMALITIES IN A HEART

(75) Inventors: Shailesh Kumar V. Musley, Blaine, MN (US); Vincent E. Splett, Apple Valley, MN (US); Aleksandre T. Sambelashvili, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 486 days.

(21) Appl. No.: 12/463,470

(22) Filed: May 11, 2009

(65) Prior Publication Data

US 2010/0286541 A1    Nov. 11, 2010

(51) Int. Cl.
*A61B 5/04* (2006.01)
(52) U.S. Cl. ........................................ 600/510
(58) Field of Classification Search .................. 600/510
See application file for complete search history.

(56) References Cited

U.S. PATENT DOCUMENTS

| 5,113,869 | A | 5/1992 | Nappholz et al. |
| 6,128,526 | A | 10/2000 | Stadler et al. |
| 6,366,812 | B1 * | 4/2002 | Levine et al. .................. 607/27 |
| 6,393,316 | B1 * | 5/2002 | Gillberg et al. ............... 600/515 |
| 7,225,015 | B1 | 5/2007 | Min et al. |
| 7,254,440 | B1 | 8/2007 | Kroll |
| 7,277,745 | B2 | 10/2007 | Natarajan et al. |
| 7,463,921 | B2 | 12/2008 | Courderc et al. |
| 2004/0127945 | A1 | 7/2004 | Collins et al. |
| 2006/0116593 | A1 | 6/2006 | Zhang et al. |
| 2006/0116596 | A1 * | 6/2006 | Zhou et al. ..................... 600/516 |
| 2007/0129639 | A1 | 6/2007 | Zhang et al. |
| 2008/0027502 | A1 * | 1/2008 | Ransom ........................... 607/42 |
| 2008/0064973 | A1 | 3/2008 | Fischell et al. |
| 2008/0177194 | A1 | 7/2008 | Zhang et al. |

OTHER PUBLICATIONS

Ninan et al., "Can Left Bundle Branch Block Cause Chest Pain", The British Journal of Cardiology, vol. 9, Issue 4, Apr. 2002, pp. 230-232.
Grom et al., "A Technical Approach to Optimized Atrial Recognition in the ICD: The Intrathoracic Six-Channel Farfield ECG", Pace, vol. 26, Jul. 2003, Part I, pp. 1472-1478.
Cannon et al., "Relationship of Symptom-Onset-to-Balloon Time and Door-to-Balloon Time With Mortality in Patients Undergoing Angioplasty for Acute Myocardial Infarction", (Reprinted) JAMA, Jun. 14, 2000, vol. 283, No. 22, pp. 2941-2947.
Prakash et al., "Clinical and Exercise Test Predictors of All-Cause Mortality", American College of CHEST Physicians (on-line), Sep. 2001, pp. 1003-1013.

(Continued)

*Primary Examiner* — Niketa Patel
*Assistant Examiner* — William Levicky
(74) *Attorney, Agent, or Firm* — Stephen W. Bauer; Michael J. Ostrom

(57) ABSTRACT

Techniques are described for detecting conduction abnormalities in a heart of a patient. In particular, an IMD may be configured to obtain electrical signals corresponding to cardiac activity of the heart of the patient and periodically analyze a most recent electrical signal of the obtained electrical signals to detect an electrical conduction abnormality of the heart. The IMD adjusts a frequency at which the most recent electrical signal is analyzed based on at least one physiological parameter of the patient. For example, the IMD may increase the frequency at which the most recent electrical signal is analyzed when a heart rate parameter has significantly changed and the number of detected premature ventricular contractions (PVCs) is greater than or equal to a threshold number. In this manner, the most recent electrical signal is analyzed at a higher frequency in situations in which conduction abnormalities are more likely.

18 Claims, 7 Drawing Sheets

OTHER PUBLICATIONS

Theres et al., "Comparison of Electrocardiogram and Intrathoracic Electrogram Signals for Detection of Ischemic ST Segment Changes During Normal Sinus and Ventricular Paced Rhythms", Reprinted with permission from Journal of Cardiovascular Electrophysiology, vol. 13, No. 10, Oct. 2002.

(PCT/US2010/031208) PCT Notification of Transmittal of the International Search Report and the Written Opinion of the International Searching Authority, Mailed Jul. 15, 2010, 9 pages.

\* cited by examiner

DETECTING ELECTRICAL CONDUCTION ABNORMALITIES IN A HEART

TECHNICAL FIELD

This disclosure relates to implantable medical devices (IMDs), and, more particularly, to detecting conduction abnormalities in a heart of a patient.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter-defibrillators (ICDs), provide therapeutic electrical stimulation to or monitor the heart of the patient via electrodes carried by one or more implantable leads. The leads are typically implanted transvenous, i.e., implanted in the heart through one or more veins, sometimes referred to as endocardial leads. Other IMDs, sometimes referred to as subcutaneous devices, may include leads that are not implanted within the heart. Instead, these leads are implanted outside of the heart and may be referred to as epicardial leads. In either case, the electrical stimulation provided by the IMD may include signals such as pacing pulses, cardiac resynchronization pulses, cardioversion shocks or defibrillation shocks to address various cardiac conditions, including bradycardia, tachycardia or fibrillation.

In some cases, the IMD senses electrical signals representative of depolarization and/or repolarization of the heart and analyzes the sensed signals to identify existence of a cardiac condition. The cardiac condition may include any of a variety of conditions including cardiac ischemia, cardiac infarction, branch bundle block, arrhythmias or the like. Upon detecting the condition, the IMD may notify a patient and/or physician of the condition or provide a therapy to the patient, e.g., an electrical stimulation therapy or a drug delivery therapy.

SUMMARY

This disclosure describes techniques for detecting conduction abnormalities in a heart of a patient. In particular, an IMD may be configured to obtain electrical signals corresponding to cardiac activity of the heart of the patient and periodically analyze a most recent electrical signal of the obtained electrical signals to monitor for an electrical conduction abnormality of the heart. The IMD adjusts the frequency at which the most recent electrical signal is analyzed based on at least one physiological parameter of the patient. For example, the IMD may increase the frequency at which the most recent electrical signal is analyzed when a heart rate parameter has significantly changed and the number of detected premature ventricular contractions (PVCs) is greater than or equal to a threshold number. In this manner, the most recent electrical signal is analyzed at a higher frequency in situations in which conduction abnormalities are more likely.

In one example, the disclosure provides an implantable medical device (IMD) comprising a sensing module configured to acquire cardiac electrical signals corresponding to cardiac activity of a heart of a patient via at least one sensor and a processor configured to obtain the cardiac electrical signals corresponding to cardiac activity of a heart of a patient, periodically analyze a most recent cardiac electrical signal of the obtained cardiac electrical signals to monitor for an electrical conduction abnormality of the heart and adjust a frequency at which the most recent electrical signal is analyzed based on at least one physiological parameter of the patient.

In another example, the disclosure provides a method comprising obtaining electrical signals corresponding to cardiac activity of a heart of a patient, periodically analyzing a most recent electrical signal of the obtained electrical signals to monitor for an electrical conduction abnormality of the heart, and adjusting a frequency at which the most recent electrical signal is analyzed based on at least one physiological parameter of the patient.

In another example, the disclosure provides a computer-readable storage medium comprising instructions that, when executed by a processor in an implantable medical device, cause the processor to obtain electrical signals corresponding to cardiac activity of a heart of a patient, periodically analyze a most recent electrical signal of the obtained electrical signals to monitor for an electrical conduction abnormality of the heart and adjust a frequency at which the most recent electrical signal is analyzed based on at least one physiological parameter of the patient.

In a further example, the disclosure provides an implantable medical device (IMD) comprising means for obtaining electrical signals corresponding to cardiac activity of a heart of a patient, means for periodically analyzing a most recent electrical signal of the obtained electrical signals to monitor for an electrical conduction abnormality of the heart, and means for adjusting a frequency at which the most recent electrical signal is analyzed based on at least one condition of the patient.

This summary is intended to provide an overview of the subject matter described in this disclosure. It is not intended to provide an exclusive or exhaustive explanation of the invention as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

In general, this disclosure describes techniques for detecting conduction abnormalities in a heart of a patient. Conduction abnormalities are changes in conduction of the heart that may be, and often are, indicative of a heart condition, such as cardiac ischemia, cardiac infarction, bundle branch block, fascicular block or other non-specific conduction disturbances. If left untreated, these heart conditions may lead to heart failure. As will be described in detail, an IMD is configured to obtain electrical signals corresponding to cardiac activity of the heart of the patient and periodically analyze a most recent electrical signal of the obtained electrical signals to monitor for an electrical conduction abnormality of the heart. The IMD adjusts a frequency at which the most recent electrical signal is analyzed based on at least one physiological parameter of the patient.

Detection and treatment of electrical conduction abnormalities of the heart early after their first occurrence can significantly improve clinical prognosis, particularly in the case of Acute Myocardial Infarction (AMI) (commonly referred to as a heart attack). In other words, reducing the amount of time until the patient receives treatment for the cardiac condition can lead to significantly better outcome. For example, early device-based detection may prevent myocardial remodeling and development of heart failure. Monitoring for conduction abnormalities with the IMD in accordance with the techniques of this disclosure may result in earlier detection of the conduction abnormalities as well as more accurate detection, e.g., reduction in false detections.

Figure 1:
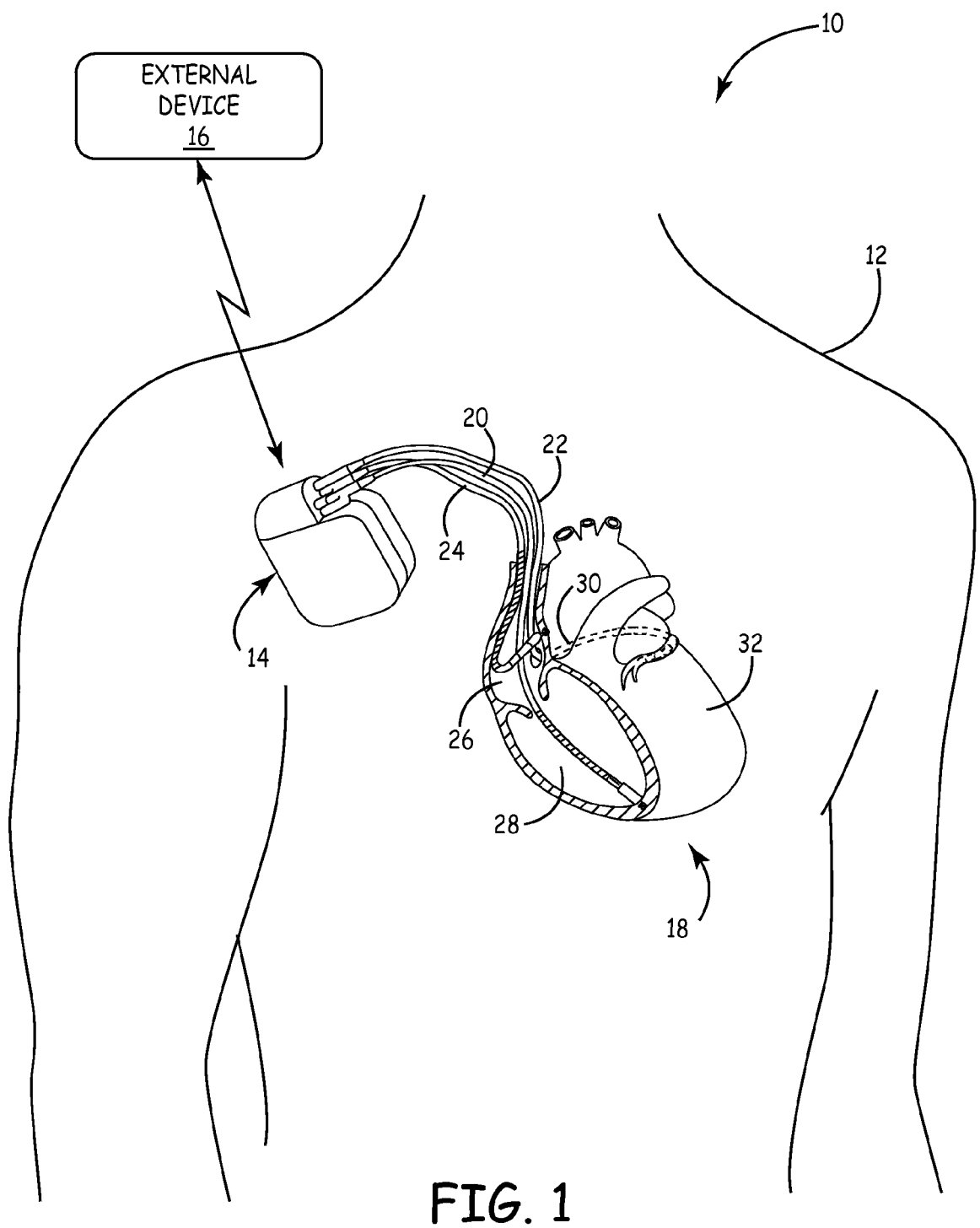
FIG. 1 is a conceptual diagram illustrating an example therapy system that may be used to provide therapy to patient.

FIG. 1 is a conceptual diagram illustrating an example therapy system 10 that may be used to provide therapy to and/or monitor a condition of patient 12. Therapy system 10 includes an IMD 14 and leads 20, 22 and 24 that extend from IMD 14. Therapy system 10 may also include an external device 16 that wirelessly communicates with IMD 14. External device 16 may, for example, comprise a programming device or a monitoring device.

In the example illustrated in FIG. 1, IMD 14 is an implantable cardiac device that is capable of providing electrical stimulation therapy to a heart 18 of patient 12. The electrical stimulation therapy to heart 18, sometimes referred to as cardiac rhythm management therapy, may include pacing, cardioversion, defibrillation and/or cardiac resynchronization therapy (CRT). As such, IMD 14 may operate as an implantable pacemaker, cardioverter, and/or defibrillator. The electrical stimulation therapy provided by IMD 14 depends on the heart condition detected by IMD 14, as described in further detail below.

IMD 14 delivers the electrical stimulation therapy to heart 18 via one or more electrodes located on leads 20, 22 and/or 24 and implanted within or adjacent to one or more atria or ventricles of heart 18. In the example illustrated in FIG. 1, leads 20, 22 and 24 are coupled to IMD 14 and extend into heart 18 of patient 12. In the example shown in FIG. 1, lead 20 is a right ventricular (RV) lead that extends through one or more veins (not shown), the superior vena cava (not shown), and right atrium 26, and into right ventricle 28 of heart 18. Lead 22 is left ventricular (LV) coronary sinus lead that extends through one or more veins, the vena cava, right atrium 26, and into the coronary sinus 30 to a region adjacent to the free wall of left ventricle 32 of heart 18. Lead 24 is a right atrial (RA) that extends through one or more veins and the vena cava, and into the right atrium 26 of heart 18. In other examples, IMD 14 may deliver stimulation therapy to heart 18 by delivering stimulation to an extravascular tissue site in addition to or instead of delivering stimulation via electrodes of intravascular leads 20, 22 and 24.

In addition to delivering therapy to heart 18, electrodes of leads 20, 22 and 24 may sense electrical signals corresponding to cardiac activity of heart 18. Electrodes of leads 20, 22 and 24 may, for example, sense electrical signals attendant to depolarization and repolarization of heart 18. IMD 14 may periodically analyze the sensed electrical signals to monitor a rhythm of heart 18 for an abnormal heart condition, such as a conduction change (abnormality) or an arrhythmia. IMD 14 may, for example, analyze an electrogram (EGM) corresponding to a most recent cardiac event (e.g., heart beat) every three hours to monitor for electrical conduction abnormalities of the heart. IMD 14 may compare the EGM corresponding to the most recent cardiac event to a template EGM to determine whether the EGM corresponding to the most recent cardiac event has changed with respect to the template EGM. IMD 14 may detect the electrical conduction abnormality when the EGM corresponding to the most recent cardiac event is significantly different than the template EGM.

IMD 14 adjusts a frequency at which (or rate at which) it analyzes the most recent electrical signal based on at least one physiological parameter of patient 12. In one instance, IMD 14 adjusts the frequency at which it analyzes the most recent EGM based on a heart rate of patient 12 and a number of detected premature ventricular contractions (PVCs). For example, IMD 14 may increase the frequency at which it analyzes the most recent electrical signal from every three hours to every hour or every half hour when the heart rate of patient 12 is greater than a heart rate threshold value and the number of detected PVCs is greater than a PVC threshold value. This is because the likelihood of heart 18 having conduction abnormalities increases when the patient has a high heart rate and large number of PVCs. Thus, IMD 14 may provide earlier detection of conduction abnormalities indicative of the heart condition by increasing the frequency at which IMD 14 analyzes the most recent electrical signal in situations in which conduction abnormalities are more likely.

In response to detecting the conduction abnormality, IMD 14 may perform one or more actions. In some instances, IMD 14 may deliver a therapy to patient 12. For example, IMD 14 may deliver electrical stimulation therapy (e.g., anti-tachycardia pacing (ATP), defibrillation shock and/or cardioversion shock) to heart 18 in response to detecting the conduction abnormality. As another example, IMD 14 and/or a different IMD may deliver drug therapy to patient 12 to treat the conduction abnormality. IMD 14 may log the detected event in memory and/or provide a patient or physician with an alert or notification of the event in addition to or instead of delivery therapy. In other words, IMD 14 may not deliver therapy to heart 18 in response to detecting the conduction abnormality.

A user, such as a physician, technician, or other clinician, may interact with external device 16 to communicate with IMD 14. For example, the user may interact with external device 16 to retrieve physiological or diagnostic information from IMD 14. For example, the user may use external device 16 to retrieve information from IMD 14 regarding the rhythm of the heart of patient 12, trends therein over time, or detected cardiac conditions. As another example, the user may use external device 16 to retrieve information from IMD 14 regarding other sensed physiological parameters of patient 12, such as electrical signals from the heart (e.g., EGM), intracardiac or intravascular pressure, activity, posture, respiration or thoracic impedance. As another example, the user may use external device 16 to retrieve information from IMD 14 regarding the performance or integrity of IMD 14 or other components of therapy system 10, such as leads or a power source of IMD 14.

The user may also interact with external device 16 to program IMD 14, e.g., select values for operational parameters of IMD 14. For electrical stimulation therapies, for example, the user may interact with external device 16 to program one or more sets of therapy parameters, select therapy programs or progressions of therapy programs to be used during particular arrhythmias, select an electrode or combination of electrodes of leads 20, 22 and 24 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes.

External device 16 may be a dedicated hardware device with dedicated software for programming of IMD 14. Alternatively, external device 16 may be an off-the-shelf computing device running an application that enables external device 16 to program IMD 14. In some examples, external device 16 may be a handheld computing device or a computer workstation. External device 16 may, in some instances, include a programming head that may be placed proximate to the patient's body near the implant site of IMD 14 in order to improve the quality or security of communication between IMD 14 and external device 16. External device 16 may include a user interface that receives input from the user and/or displays data to the user.

External device 16 may communicate with IMD 14 via wireless communication using any techniques known in the art. Examples of communication techniques may include, for example, magnetic telemetry, low frequency telemetry or radiofrequency (RF) telemetry, but other techniques are also contemplated. In some instances, external device 16 and IMD 14 may communicate in accordance with the Medical Implant Communications Service (MICS) protocol or the Medical Electronic Data Services (MEDS) protocol.

Although FIG. 1 is described in the context of providing therapy to patient 12, the techniques of this disclosure may be used in IMDs that do not provide therapy to a patient. As one example, the techniques of this disclosure may be used in an IMD that only provides monitoring of patient 12, such as an implantable loop recorder.

Figure 2:
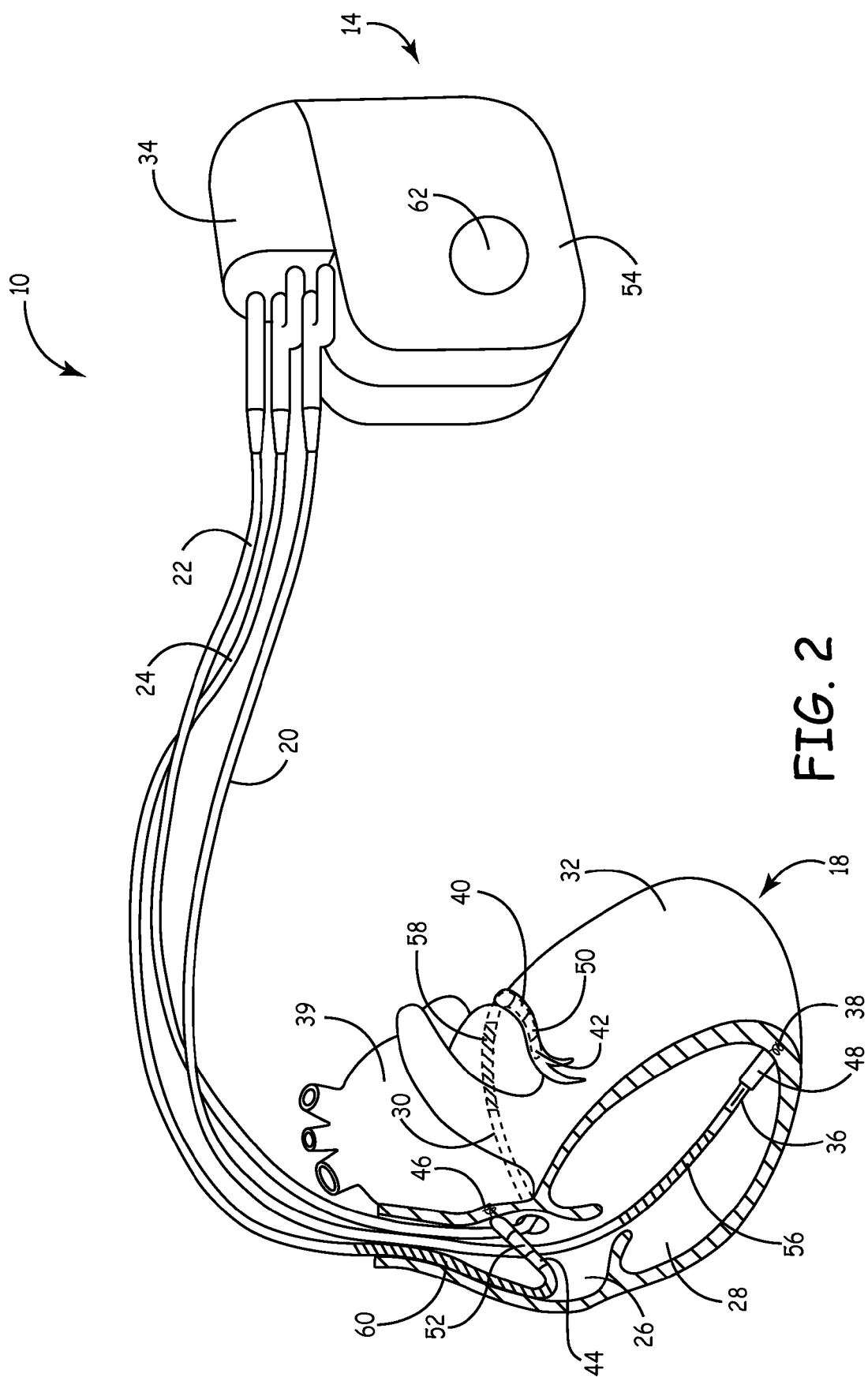
FIG. 2 is a conceptual diagram illustrating an implantable medical device (IMD) and leads of the therapy system of FIG. 1 in greater detail.

FIG. 2 is a conceptual diagram illustrating IMD 14 and leads 20, 22 and 24 of therapy system 10 in greater detail. Leads 20, 22 and 24 are electrically coupled to a therapy module, a sensing module, or other modules of IMD 14 via connector block 34. In some examples, proximal ends of leads 20, 22 and 24 include electrical contacts that electrically couple to respective electrical contacts within connector block 34. In addition, in some examples, leads 20, 22 and 24 are mechanically coupled to connector block 34 with the aid of set screws, connection pins or another suitable mechanical coupling mechanism.

Each of the leads 20, 22 and 24 includes an elongated insulative lead body, which may carry a number of concentric coiled conductors separated from one another by tubular insulative sheaths. Other lead configurations are also contemplated, such as lead configurations that do not include coiled conductors, but instead a different type of conductor. In the illustrated example, bipolar electrodes 36 and 38 are located proximate to a distal end of lead 20. In addition, bipolar electrodes 40 and 42 are located proximate to a distal end of lead 22 and bipolar electrodes 44 and 46 are located proximate to a distal end of lead 24.

Electrodes 36, 40, and 44 may take the form of ring electrodes, and electrodes 38, 42, and 46 may take the form of extendable helix tip electrodes mounted retractably within insulative electrode heads 48, 50, and 52, respectively. Each of the electrodes 36, 38, 40, 42, 44, and 46 is electrically coupled to a respective one of the conductors within the lead body of its associated lead 20, 22 and 24, and thereby coupled to respective ones of the electrical contacts on the proximal end of leads 20, 22 and 24. In other embodiments, electrodes 36, 38, 40, 42, 44, and 46 may be other types of electrodes.

Electrodes 36, 38, 40, 42, 44, and 46 may sense electrical signals attendant to the depolarization and repolarization of heart 18. The electrical signals are conducted to IMD 14 via the one or more conductors of respective leads 20, 22 and 24. In some examples, IMD 14 also delivers pacing pulses via electrodes 36, 38, 40, 42, 44, and 46 to cause depolarization of cardiac tissue of heart 14. In some examples, as illustrated in FIG. 2, IMD 14 includes one or more housing electrodes, such as housing electrode 62, which may be formed integrally with an outer surface of hermetically-sealed housing 54 of IMD 14 or otherwise coupled to housing 54. In some examples, housing electrode 62 is defined by an uninsulated portion of an outward facing portion of housing 54 of IMD 14. In some examples, housing electrode 62 comprises substantially all of housing 54. Divisions between insulated and uninsulated portions of housing 54 may be employed to define two or more housing electrodes. Any of the electrodes 36, 38, 40, 42, 44, and 46 may be used for unipolar sensing or pacing in combination with housing electrode 62. As such, the configurations of electrodes used by IMD 14 for sensing and pacing may be unipolar or bipolar depending on the application.

Leads 20, 22 and 24 also include elongated electrodes 56, 58, and 60, respectively, which may, in some instances, take the form of a coil. IMD 14 may deliver high energy electrical shocks, e.g., defibrillation or cardioversion shocks, to heart 18 via any combination of elongated electrodes 56, 58, and 60, and housing electrode 62. In particular, IMD 14 may deliver the high energy electrical shocks in response to determining that a detected arrhythmia is treatable. Electrodes 36, 38, 40, 42, 44, 46, 56, 58, 60, and 62 may be fabricated from any suitable electrically conductive material, including, but not limited to, platinum, platinum alloy or other materials known to be usable in implantable defibrillation electrodes.

The configuration of therapy system 10 illustrated in FIGS. 1 and 2 are merely examples. In other examples, therapy system 10 may include more or fewer leads extending from IMD 14. For example, IMD 14 may be coupled to two leads, e.g., one lead implanted within right atrium 26 and the other implanted within right ventricle 28. In another example, IMD 14 may be coupled to a single lead that is implanted within either an atrium or ventricle of heart 18. As a further example, the therapy system may include three transvenous leads located as illustrated in FIGS. 1 and 2, and an additional lead located within or proximate to left atrium 32. As such, IMD 14 may be used for single chamber or multi-chamber cardiac rhythm management therapy. In addition to more or fewer leads, each of leads 20, 22 and 24 may include more or fewer electrodes.

In still other examples, a therapy system may include epicardial leads and/or patch electrodes instead of or in addition to the transvenous leads 20, 22 and 24 illustrated in FIGS. 1 and 2. In other words, IMD 14 may be a subcutaneous cardiac device. Further, IMD 14 need not be implanted within patient 12. In examples in which IMD 14 is not implanted in patient 12, IMD 14 may deliver defibrillation pulses and other therapies to heart 18 via percutaneous leads that extend through the skin of patient 12 to a variety of positions within or outside of heart 18.

Figure 3:
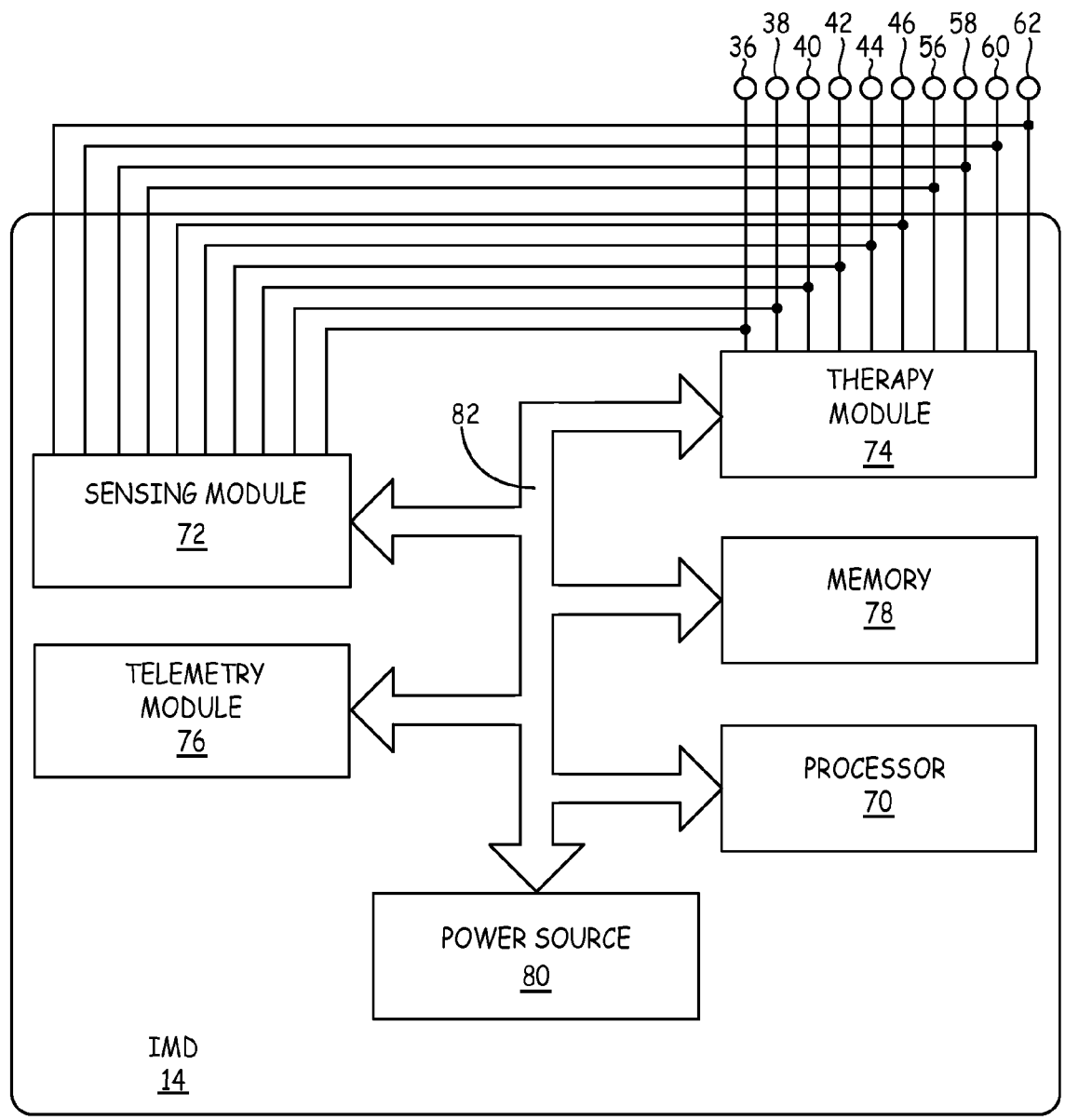
FIG. 3 is a functional block diagram of an example configuration of components of an IMD.

FIG. 3 is a functional block diagram of an example configuration of components of IMD 14. In the example illustrated by FIG. 3, IMD 14 includes a processor 70, sensing module 72, therapy module 74, telemetry module 76, memory 78, and power source 80. The various components of IMD 14 are interconnected by a data bus 82. In other examples, the various components of IMD 14 may be interconnected by a number of point-to-point connections or a combination of one or more data buses and one or more point-to-point connections.

Processor 70 may include one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Memory 78 may include computer-readable instructions that, when executed by processor 70, cause components of IMD 14 to perform various functions attributed to the respective components in this disclosure. Memory 78 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The various components of IMD 14 are coupled to power source 80, which may include a non-rechargeable battery, rechargeable storage device such as a rechargeable battery or capacitor (which may be recharged internally or transcutaneously with the use of electromagnetic or piezoelectric transformers), energy-harvesting device, or a combination thereof. A non-rechargeable battery may be capable of holding a charge for several years, while a rechargeable battery may be inductively charged from an external device, e.g., on a daily or weekly basis. Power source 80 also may include power supply circuitry (not shown in FIG. 3) for providing regulated voltage and/or current levels to power the components of IMD 14.

Processor 70 controls therapy module 74 to deliver therapy, such as stimulation therapy or drug therapy, to heart 18. Processor 70 may control therapy module 74 to deliver therapy (e.g., electrical stimulation therapy, drug therapy, or a combination thereof) according to a selected one or more therapy programs, which may be stored in memory 78. For example, processor 70 may control therapy module 74 to deliver electrical pacing pulses, cardiac resynchronization pulses, or cardioversion or defibrillation shocks with the amplitudes, pulse widths, frequencies, and/or electrode polarities specified by the selected therapy programs. In this case, therapy module 74 may include an electrical stimulation generator. As another example, processor 70 may control therapy module 78 to deliver one or more drugs, such as antiplatelets (aspirin), beta blockers, calcium channel blockers, or ACE inhibitors, to patient 12 in dosages specified by the selected therapy programs. In this case, therapy module 74 may include a pump coupled to a delivery catheter. The type of therapy program provided may, for example, be dependent on the type of heart condition detected, whether a previous therapy program was effective, or the like.

Therapy module 74 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14 for delivering electrical stimulation therapy. Therapy module 74 may include a switch module (not shown in FIG. 3) and processor 70 may use the switch module to select, e.g., via a data/address bus 82, which of the available electrodes to use to deliver pacing, resynchronization, cardioversion, or defibrillation pulses/shocks. The switch module may include a switch array, switch matrix, multiplexer, or any other type of switching device suitable to selectively couple stimulation energy to selected electrodes. Therapy module 74 may also be coupled to a delivery catheter in the case of drug therapy.

Sensing module 72 is configured to receive electrical signals sensed by one or more sensors connected to sensing module 72. The electrical signals sensed by the one or more sensors may include cardiac events, such as electrical signals attendant to depolarization and repolarization of heart 18. Sensing module 72 is electrically coupled to electrodes 36, 38, 40, 42, 44, 46, 56, 58, 60, and 62, e.g., via conductors of the respective lead 20, 22 and 24, or, in the case of housing electrode 62, via an electrical conductor disposed within housing 54 of IMD 14. In this case, electrodes 36, 38, 40, 42, 44, 46, 56, 58, 60, and 62 are the sensors connected to sensing module 72. Sensing module 72 may include a switch module and processor 80 may use the switch module to select, e.g., via a data/address bus 82, which of the available electrodes are used to sense electrical cardiac signals of heart 18. In this manner, sensing module 72 is capable of monitoring signals from a variety of electrode sensing vectors formed by different combinations of electrodes 36, 38, 40, 42, 44, 46, 56, 58, 60, and 62, including both bipolar and unipolar sensing vectors. The switch module may include a switch array, switch matrix, multiplexer, or any other type of switching device suitable to selectively couple the selected electrodes to the sensing circuitry of sensing module 72. In some instances, sensing module 72 and therapy module 74 may share a switch module and/or may be a common component.

Sensing module 72 may receive signals sensed by various other sensors instead of, or in addition to, the signals sensed by the combinations of electrodes 36, 38, 40, 42, 44, 46, 56, 58, 60 and 62. For example, sensing module 72 may receive signals from one or more sensors that sense intravascular pressure, blood pressure, blood flow, acceleration, displacement, motion, respiration, or blood/tissue chemistry such as oxygen saturation, carbon dioxide, pH, protein levels, enzyme levels or other physiological parameter. Sensing module 72 may couple to these various other sensors via a wired connection or a wireless connection, e.g., using telemetry module 76.

Sensing module 72 may store the sensed signals in memory 78. In some instances, sensing module 72 may store the sensed signals in raw form. In other instances, sensing module 72 may process the sensed signals and store the processed signals in memory 78. For example, sensing module 72 may amplify and filter the sensed signal and store the filtered signal in memory 78.

The signals stored by sensing module 72 may be retrieved and further processed by processor 70. For example, processor 70 may periodically retrieve the most recent cardiac electrical signal and analyze the retrieved cardiac electrical signal to monitor for electrical conduction abnormalities indicative of a heart condition of patient 12. IMD 14 may analyze an EGM or a portion of an EGM corresponding to a most recent cardiac event. IMD 14 may, for instance, analyze an ST segment of the EGM, a T-wave segment of the EGM, a QRS segment of the EGM, other segment of the EGM or a combination of various segments of the EGM.

IMD 14 may analyze the EGM by comparing the EGM corresponding to the most recent cardiac event (also referred to herein as the most recent EGM) to a template EGM to determine whether the most recent EGM corresponding to the most recent cardiac event has significantly changed with respect to the template EGM. The template EGM may be an EGM corresponding to a cardiac event during a known normal sinus rhythm or a known abnormal sinus rhythm. IMD 14 may detect the electrical conduction abnormality when the EGM corresponding to the most recent cardiac event is significantly different than the template EGM. This is because the electrical conduction abnormalities result in significant changes in the morphology of the EGM or at least portions of the EGM, such as ST segment, T-wave segment and QRS segment.

Processor 70 may compare the most recent EGM to the template EGM to generate a matching metric. Processor 70 may compare the matching metric to a matching threshold value to determine whether a morphology of the EGM of the most recent cardiac event has significantly changed compared to the template EGM. For instance, processor 70 may determine that the morphology of the most recent EGM has significantly changed when the matching metric falls below a threshold value.

Processor 70 may perform the morphology analysis using a wavelet transform of the most recent EGM. One example technique for performing wavelet transforms on EGMs is described in U.S. Pat. No. 6,393,316 to Gillberg et al. ("the '316 patent"), which is incorporated herein by reference in its entirety. A wavelet transform is a mechanism for describing the evolution over time of signal frequency. The wavelet transform method performs "template matching," which is a mathematical comparison of a template EGM, e.g., of a cardiac event during normal sinus rhythm, to the EGM of the most recent cardiac event to generate a matching metric. The matching metric in this case may be referred to as a wavelet matching score. The wavelet matching score generated by the template matching may take on a value between 0 and 100, with larger wavelet matching scores corresponding to a closer match between the EGM of the most recent cardiac event and the template EGM.

Processor 70 determines that the EGM of the most recent cardiac event has not significantly changed when the wavelet matching score is greater than or equal to seventy, and determines that the EGM of the most recent cardiac event has significantly changed when the wavelet matching score is less than seventy. Other threshold values may be used instead of seventy. A significant change in the morphology of the EGM, and particularly the ST segment or T-wave segment of the EGM, is often indicative of conduction abnormalities associated with ischemia, infarction, branch bundle block, fascicular block or other non-specific conduction disturbances or other heart condition. Alternatively, processor 70 may use other methods for comparing waveforms to generate the matching metric, including other temporal and/or frequency domain analysis. The '316 patent, for example, also describes other techniques using an area of distance or a correlation waveform analysis metric.

In other instances, processor 70 performs the morphology analysis of the most recent EGM by analyzing one or more beat morphology parameters instead of or in addition to the matching metric. The beat morphology parameters may include a peak value associated with an ST segment or a T-wave, a slope associated with the ST segment or T-wave segment or the like. Processor 70 may determine a significant change in the most recent EGM has occurred when one or more of the beat morphology parameters has changed by a threshold value, changed polarities, or the like. Other types of beat morphology parameters may also be used in addition to or instead of the beat morphology parameters listed above.

In any case, processor 70 analyzes the EGM corresponding to the most recent cardiac event on a periodic basis, for example, once every three hours. Processor 70 may adjust a rate (or frequency) at which it analyzes the most recent electrical signal in situations in which conduction abnormalities are more likely to occur. For example, processor 70 may adjust the frequency at which it analyzes the most recent electrical signal based on one or more physiological parameters of patient 12. The physiological parameters may include a heart rate, a relative change in the heart rate, a change in variance of the heart rate, a number of PVCs or other cardiac parameter. Processor 70 may compute the one or more physiological parameters using the sensed electrical signals. Some example techniques for computing the physiological parameters are described in copending U.S. patent application Ser. No. 12/430,301, titled "DISTINGUISHING BETWEEN TREATABLE AND NON-TREATABLE HEART RHYTHMS," to Zhang et al. and U.S. Pat. No. 6,567,691 to Stadler, both of which are incorporated herein by reference in their entirety.

In one instance, processor 70 adjusts the frequency at which it analyzes the most recent EGM based on a heart rate of patient 12 and a number of detected premature ventricular contractions (PVCs). For example, processor 70 may increase the frequency at which it analyzes the most recent electrical signal from an initial frequency, e.g., every three hours to an increased frequency, e.g., every hour or every half hour, when the heart rate of patient 12 is greater than a heart rate threshold value (e.g., 90 beats per minute (bpm)) and the number of detected PVCs is greater than a PVC threshold value (e.g., 10 PVCs per hour). The threshold values of 90 bpm and 10 PVCs per hour are provided for illustration purposes only. The values of the heart rate threshold and the PVC threshold may take on values greater than or less than the provided example values. This is because the likelihood of heart 18 having conduction abnormalities increases when patient 12 has a high or changing heart rate and large number of PVCs. Processor 70 may incrementally adjust the frequency at which it analyzes the most recent EGM based on the one or more physiological parameters. When adjusting the frequency at which processor 70 analyzes the most recent EGM based on heart rate and the number of detected PVCs, for example, processor 70 may adjust the frequency at which it analyzes the most recent EGM from a first frequency to a second, faster frequency in response to the heart rate exceeding the threshold heart rate. Processor 70 may further adjust the frequency at which it analyzes the most recent EGM from the second frequency to a third frequency that is even faster than the second frequency in response to the number of detected PVCs exceeding the PVC threshold.

Processor 70 may also increase the frequency at which it analyzes the most recent electrical signal based on the relative change in heart rate and the number of PVCs or the change in variability of the heart rate and the number of PVCs. For example, processor 70 may increase when the relative change of the rate exceeds a relative change threshold value (e.g., increased by 20 bpm within an hour) and the number of PVCs exceeds the PVC threshold (e.g., 10 PVCs per hour). As another example, processor 70 may increase when the variability is less than a variability threshold value (e.g., standard deviation of normal to normal RR intervals (SDNN)<70 ms) and the number of PVCs exceeds the PVC threshold (e.g., 10 PVCs per hour). Processor 70 may also adjust the frequency at which it analyzes the most recent electrical signal using one or more non-cardiac physiological parameters, such as respiration, pressure, activity level or the like, in addition to or instead of the cardiac physiological parameters. Moreover, processor 70 may consider one or more non-physiological parameters, such as a time of day, in making the adjustment to the frequency of analysis.

After adjusting the frequency at which processor 70 analyzes the most recent EGM, processor 70 may eventually return to the initial periodic analysis rate. Processor 70 may, for example, begin analyzing the most recent EGM at the initial frequency (e.g., every three hours) after a particular amount of time has elapsed since being adjusted to the increased frequency of analysis. Alternatively, processor 70 may return to analyzing the most recent EGM at the initial frequency (e.g., every three hours) based on the one or more physiological parameters, e.g., after a heart rate has fallen below the threshold heart rate or a different threshold heart rate. In other instances, processor 70 may incrementally decrease the frequency at which it analyzes the most recent EGM until it reaches the initial analysis frequency.

In response to detecting the conduction abnormality, IMD 14 may perform one or more actions. In some instances, IMD 14 may deliver a therapy to patient 12. For example, IMD 14 may deliver electrical stimulation therapy (e.g., anti-tachycardia pacing (ATP), defibrillation shock and/or cardioversion shock) to heart 18 in response to detecting the conduction abnormality. As another example, IMD 14 and/or a different IMD may deliver drug therapy to patient 12 to treat the conduction abnormality.

IMD 14 may perform other actions in addition to or instead of delivering therapy in response to detecting the conduction abnormality. For example, IMD 14 may log the detected event in memory 78 for later transmission and analysis by a physician. As another example, IMD 14 may alert a patient of the heart condition so that the patient may seek medical attention. IMD 14 may, for example, include means for producing the alert for patient 12, such as means for producing a beep, a vibration or the like. As a further example, IMD 14 may send a communication to external device 16 (FIG. 1) to notify a physician or clinician of the conduction abnormality.

Processor 70 may select the particular action to perform based on the amount of difference between the most recent EGM and the template EGM. For example, processor 70 may log the detected event in memory 78 if the matching metric is within a first range (e.g., fifty to seventy). Processor 70 may log the detected event as well as notify patient 12, e.g., via a vibration or beeping, if the matching metric falls below fifty.

Processor 70 may control telemetry module 76 to send the signals stored by sensing module 72 to another device, such as external device 16 of FIG. 1. Under the control of processor 70, telemetry module 76 may receive data from and send data to external device 16 (or other external or implanted device) with the aid of an antenna, which may be internal and/or external to IMD 14. Telemetry module 76 includes any suitable hardware, firmware, software or any combination thereof for communicating with another device. For example, telemetry module 76 may include appropriate modulation, demodulation, frequency conversion, filtering, and amplifier components for transmission and reception of data.

Figure 4A:
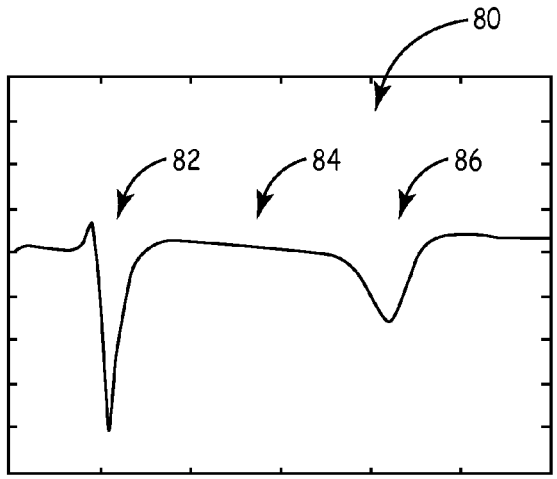
FIG. 4A-4C are a timing diagram illustrating electrograms (EGMs) of respective cardiac events.
Figure 4B:
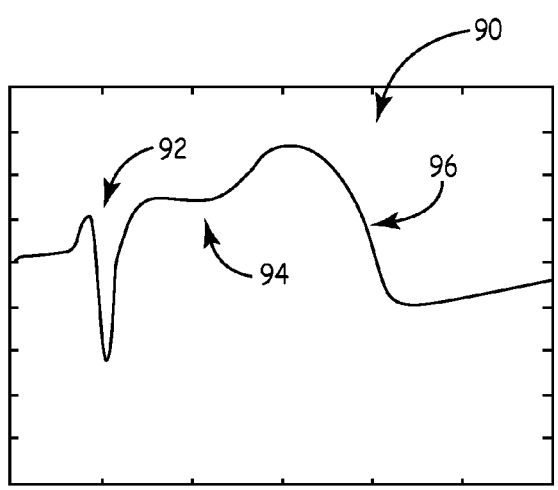
Figure 4C:
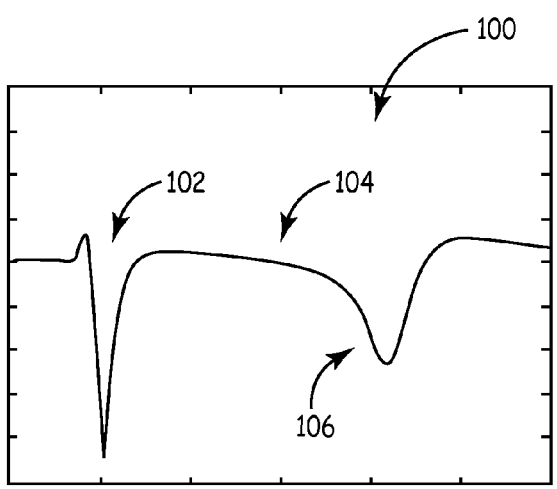

FIGS. 4A-4C are timing diagrams illustrating example EGMs of respective cardiac events. FIG. 4A is a timing diagram of an EGM 80 corresponding to a cardiac event during a normal sinus rhythm. EGM 80 includes a QRS segment 82, an ST segment 84 and a T-wave segment 86. FIG. 4B is a timing diagram of an EGM 90 corresponding to a cardiac event during an electrical conduction abnormality. In particular, EGM 90 corresponds to a cardiac event during an occlusion of Left Anterior Descending (LAD) coronary artery with a balloon catheter. EGM 90 includes a QRS segment 92, an ST segment 94 and a T-wave segment 96. FIG. 4C is a timing diagram of an EGM 100 corresponding to a cardiac event during reperfusion. EGM 100 includes a QRS segment 102, an ST segment 104 and a T-wave segment 106.

As illustrated in timing diagrams of FIGS. 4A-4C, EGM 90 during an electrical conduction abnormality substantially changes with respect to EGMs 80 and 100 during normal sinus rhythm and reperfusion, respectively. Each of the various segments, and particularly ST segment and T-wave segment, are significantly different during the electrical conduction abnormality. As such, the analysis of the most recent EGM may involve comparing one or more of the particular segments to respect segments of a template EGM to determine whether a significant change in the EGM has occurred. One of EGMs 80 or 100 may serve as the template EGM to which the EGM of a most recent cardiac event is compared. As described above, when a significant change in the EGM has occurred, IMD 14 determines that an electrical conduction abnormality exists.

EGM 90 of FIG. 4B illustrates corresponds to a cardiac event during an occlusion of Left Anterior Descending (LAD) coronary artery with a balloon catheter for purposes of illustration. Although other electrical conduction abnormalities may not produce EGMs similar to EGM 90, the EGMs produced by other electrical conduction abnormalities will still differ significantly from the template EGM.

Figure 5:
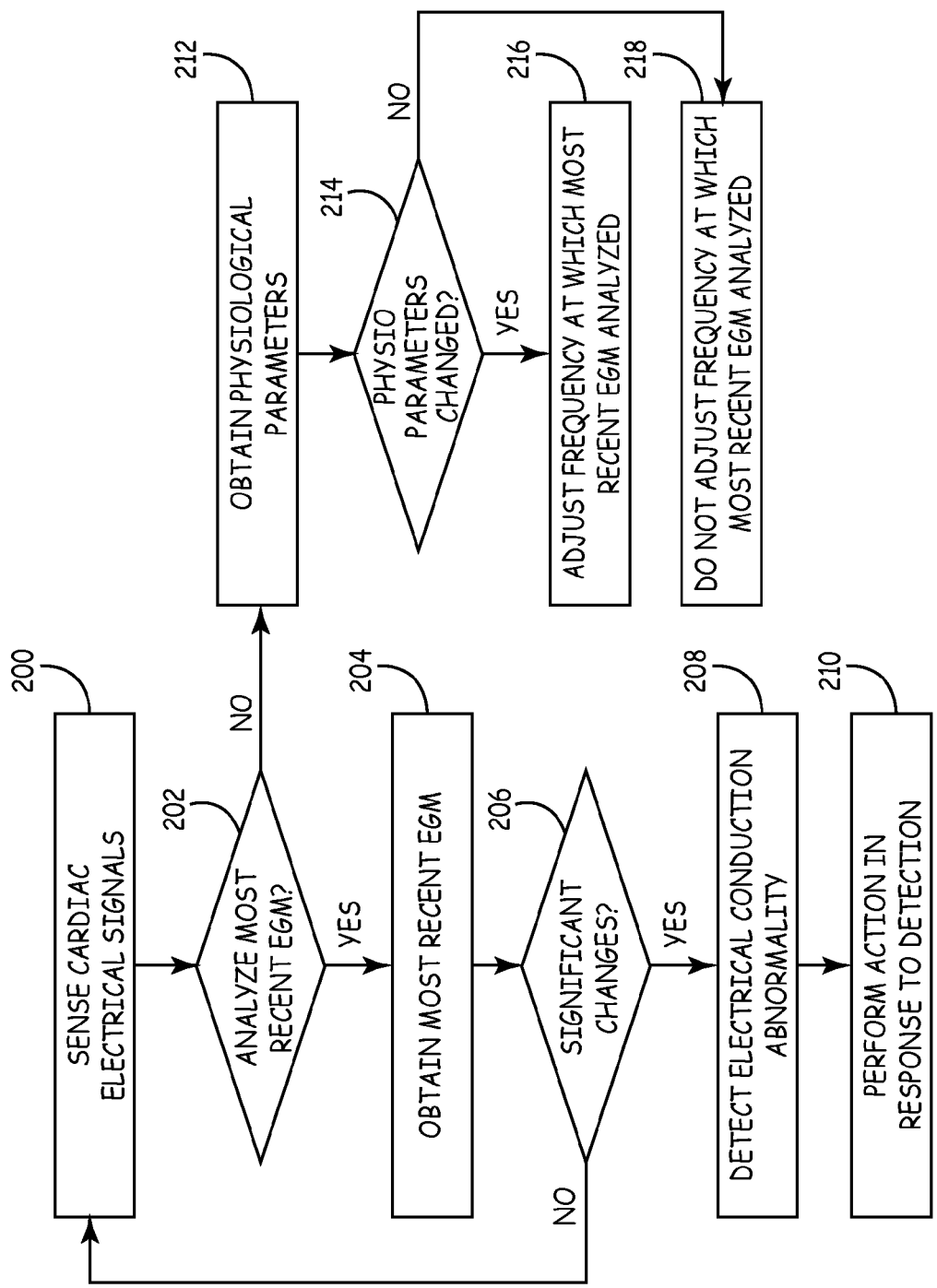
FIG. 5 is a flow diagram illustrating example operation of an IMD performing the conduction abnormality detection techniques of this disclosure.

FIG. 5 is a flow diagram illustrating example operation of an IMD, such as IMD 14, performing the conduction abnormality detection techniques of this disclosure. Sensing module 72 is configured to receive cardiac electrical signals sensed by one or more sensors connected to sensing module 72 (200). Processor 70 determines whether to analyze an EGM of the most recent cardiac electrical signal (202). As described above, processor 70 may periodically analyze the most recent EGM to monitor for electrical conduction abnormalities indicative of a heart condition of patient 12. In one example, processor 70 may analyze the most recent EGM every three hours.

When processor 70 determines to analyze the most recent EGM ("YES" branch of 202), e.g., three hours have expired since last analyzing the most recent EGM, processor 70 obtains the most recent EGM (204) and determines whether the most recent EGM has significantly changed with respect to a template EGM (204). IMD 14 may, for example, compare the most recent EGM to generate a matching metric and determine that the most recent EGM has significantly changed when the matching metric falls below a matching threshold value. In other instances, processor 70 performs the comparison of one or more beat morphology parameters, such as a peak value associated with an ST segment or a T-wave, a slope associated with the ST segment or T-wave segment or the like, instead of or in addition to the matching metric.

When processor 70 determines that the most recent EGM has not significantly changed with respect to the template EGM ("NO" branch of 206), processor 70 continues to sense cardiac electrical signals. When processor 70 determines that the most recent EGM significantly changed with respect to a template EGM ("YES" branch of 206), processor 70 detects an electrical conduction abnormality (208) and performs one or more actions (210). For example, IMD 14 may deliver a therapy to patient 12, such as stimulation therapy and/or drug therapy. As another example, IMD 14 may log the detected event in memory 78 and/or provide patient 12 or physician with an alert or notification of the event in addition to or instead of delivery therapy. In some instances, processor 70 may select the particular action to perform based on the amount of difference between the most recent EGM and the template EGM. For example, processor 70 may only log the detected event in memory 78 if the matching metric is within a first range (e.g., fifty to seventy), but log the detected event and notify patient 12, e.g., via a vibration or sound, if the matching metric falls below fifty.

When processor 70 determines to not analyze the most recent EGM ("NO" branch of 202), e.g., three hours have not expired since the last time the most recent EGM was analyzed, processor 70 obtains one or more physiological parameters (212). The physiological parameters may include a heart rate parameter (such as heart rate, a relative change in heart rate or a change in variance of the heart rate), a number of PVCs or other cardiac parameter or non-cardiac parameter. Processor 70 determines whether the physiological parameters have significantly changed with respect to respective thresholds (214). For example, processor 70 may compare a heart rate and a number of detected PVCs to respective thresholds.

When the physiological parameters have not significantly changed with respect to respective thresholds ("NO" branch of 214), processor 70 does not adjust the frequency at which it analyzes the most recent electrical signal (218). When the physiological parameters have changed with respect to respective thresholds ("YES" branch of 214), e.g., the heart rate exceeds a heart rate threshold and the number of detected PVCs exceeds a PVC threshold, processor 70 increases the frequency at which it analyzes the most recent electrical signal (216). For purposes of illustration, processor 70 may increase the frequency at which the most recent EGM is analyzed from every three hours to every hour. Other initial and/or increased frequencies may be used however. In this manner, processor 70 increases the frequency at which the most recent EGM is analyzed in situations in which conduction abnormalities are more likely to occur.

After adjusting the frequency at which processor 70 analyzes the most recent EGM, processor 70 may eventually return to the initial periodic analysis frequency. Processor 70 may, for example, begin analyzing the most recent EGM at the initial frequency (e.g., every three hours) after a particular amount of time has elapsed since being adjusted to the increased frequency of analysis. Alternatively, processor 70 may return to analyzing the most recent EGM at the initial frequency (e.g., every three hours) based on the one or more physiological parameters, e.g., after a heart rate has fallen below the threshold heart rate or a different threshold heart rate. In other instances, processor 70 may incrementally decrease the frequency at which it analyzes the most recent EGM until it reaches the initial analysis frequency.

Figure 6:
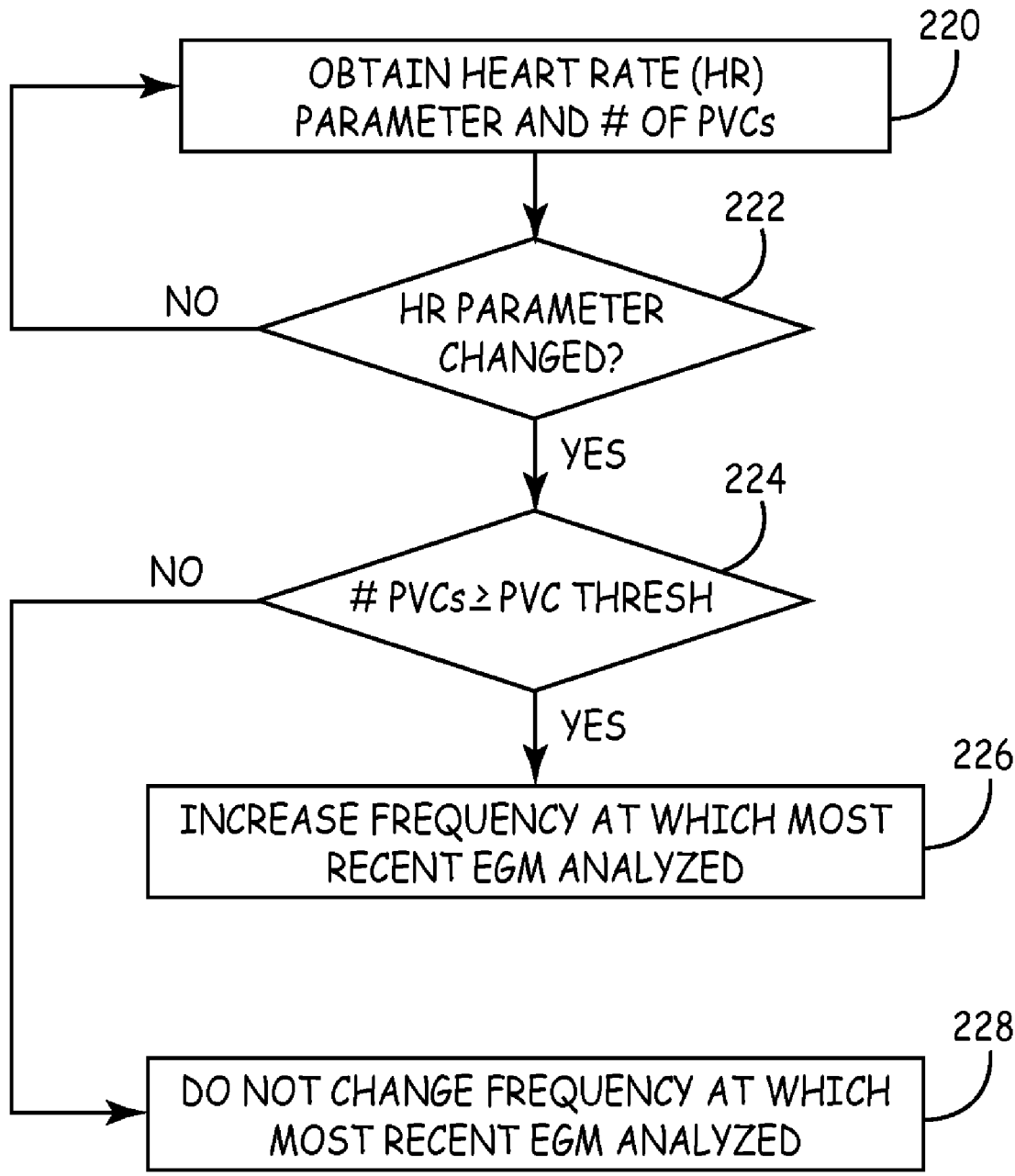
FIG. 6 is a flow diagram illustrating an example operation of an IMD adjusting a frequency at which a most current EGM is analyzed based on one or more physiological parameters.

FIG. 6 is a flow diagram illustrating an example operation of an IMD, such as IMD 14, adjusting a frequency at which a most current EGM is analyzed based on one or more physiological parameters. Processor 70 of IMD 14 obtains a heart rate parameter and a number of detected PVCs (220). Processor 70 may obtain these parameters from memory 78. As described above, the heart rate parameter may be a heart rate, a relative change in heart rate or a change in variance of the heart rate.

Processor 70 determines whether the heart rate parameter has significantly changed relative to a threshold (222). Processor 70 may, for example, determine the heart rate parameter has significantly changed when the heart rate parameter is greater than a threshold value, in the case of a heart rate or a relative change in heart rate. As another example, processor 70 may determine the heart rate parameter has significantly changed when the heart rate parameter is less than a threshold value, in the case of a variance in heart rate.

When processor 70 determines that the heart rate parameter has not significantly changed ("NO" branch of 222), processor 70 continues to obtain the physiological parameters. When processor 70 determines that the heart rate parameter has significantly changed ("YES" branch of 222), processor 70 determines whether the number of detected PVCs is greater than or equal to a threshold PVC value (224).

When processor 70 determines the number of detected PVCs is greater than or equal to the threshold PVC value ("YES" branch of 224), processor 70 increases the frequency at which it analyzes the most recent EGM (226). For purposes of illustration, processor 70 may increase the frequency at which it analyzes the most recent EGM from an initial frequency, e.g., every three hours, to an increased frequency, e.g., every hour or every half hour. This is because the likelihood of heart 18 having conduction abnormalities increases when patient 12 has a high or changing heart rate and large number of PVCs. When processor 70 determines the number of detected PVCs is not greater than or equal to the threshold PVC value ("NO" branch of 224), processor 70 does not change the frequency at which it analyzes the most recent EGM (228).

Figure 7:
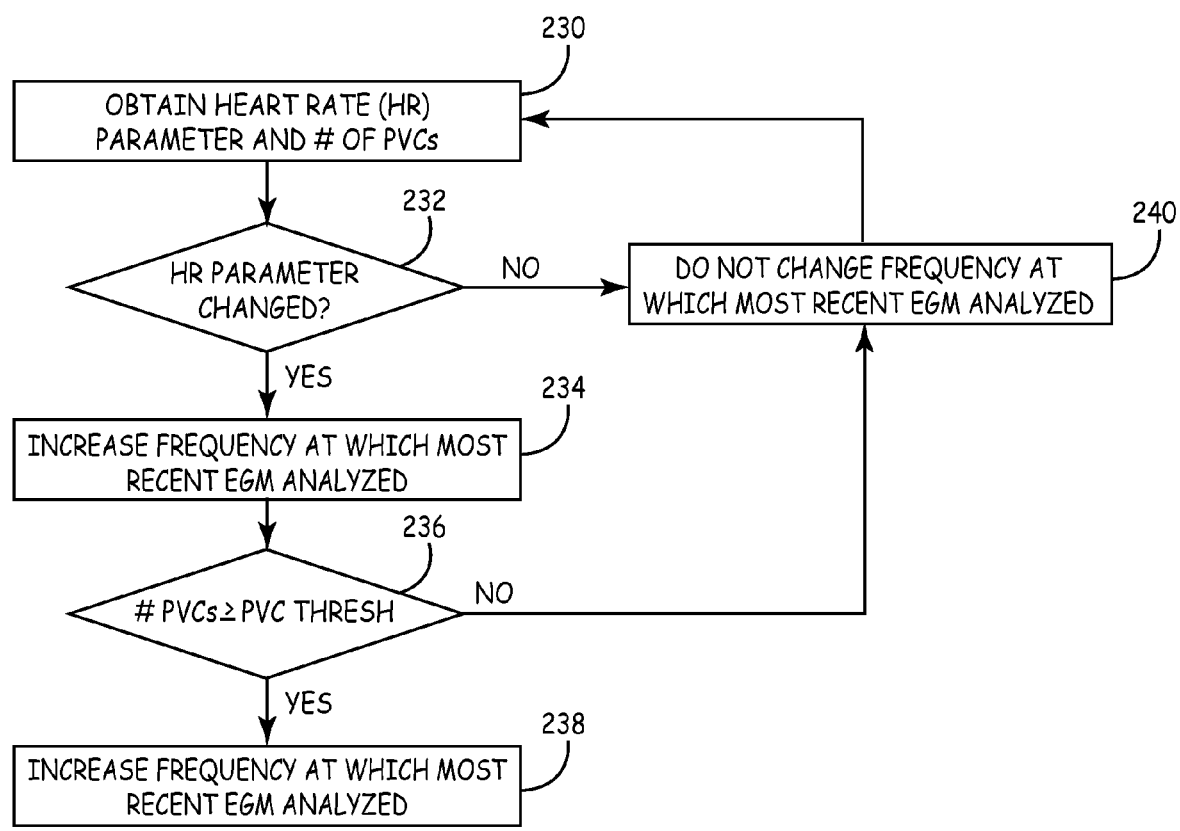
FIG. 7 is a flow diagram illustrating another example operation of an IMD adjusting a frequency at which a most current EGM is analyzed based on one or more physiological parameters.

FIG. 7 is a flow diagram illustrating another example operation of an IMD, such as IMD 14, adjusting a frequency at which a most current EGM is analyzed based on one or more physiological parameters. Processor 70 of IMD 14 obtains a heart rate parameter and a number of detected PVCs (230). Processor 70 may obtain these parameters from memory 78. Processor 70 determines whether the heart rate parameter has significantly changed relative to a threshold (232). Processor 70 may, for example, determine the heart rate parameter has significantly changed when the heart rate parameter is greater than a threshold value, in the case of a heart rate or a relative change in heart rate. As another example, processor 70 may determine the heart rate parameter has significantly changed when the heart rate parameter is less than a threshold value, in the case of a variance in heart rate.

When processor 70 determines that the heart rate parameter has not significantly changed ("NO" branch of 232), processor 70 does not change the frequency at which it analyzes the most recent EGM (240). When processor 70 determines that the heart rate parameter has significantly changed ("YES" branch of 232), processor 70 increases the frequency at which it analyzes the most recent EGM to a first increased frequency (234). Processor 70 then determines whether the number of detected PVCs is greater than or equal to a threshold PVC value (224).

When processor 70 determines the number of detected PVCs is not greater than or equal to the threshold PVC value ("NO" branch of 236), processor 70 does not change the frequency at which it analyzes the most recent EGM (240). In other words, processor 70 continues to periodically analyze the most recent EGM at the first increased frequency. When processor 70 determines the number of detected PVCs is greater than or equal to the threshold PVC value ("YES" branch of 224), processor 70 increases the frequency at which it analyzes the most recent EGM to a second increased frequency that is faster than the first increased frequency (238). In this manner, processor 70 may incrementally adjust the frequency at which it analyzes the most recent EGM based on the one or more physiological parameters.

The techniques described in this disclosure, including those attributed to IMD 14 or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete digital, analog or logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. However, these examples should not be considered limiting of the techniques as described herein. These and other examples are within the scope of the following claims.

The invention claimed is:

1. An implantable medical device (IMD) comprising:
a sensing module configured to acquire cardiac electrical signals corresponding to cardiac activity of a heart of a patient via at least one sensor; and
a processor configured to obtain the cardiac electrical signals corresponding to cardiac activity of the heart of the patient, periodically analyze, at a first frequency, a most recent cardiac electrical signal of the obtained cardiac electrical signals to monitor for an electrical conduction abnormality of the heart, compute at least a heart rate parameter of the patient and a number of premature ventricular contractions (PVCs) using the acquired cardiac electrical signals, compare the heart rate parameter of the patient to a heart rate parameter threshold, compare the number of PVCs to a PVC threshold, and increase the frequency at which the most recent electrical signal is analyzed to a second frequency when the heart rate parameter of the patient is greater than the heart rate parameter threshold and the number of PVCs detected is greater than the PVC threshold, wherein the first frequency and the second frequency are greater than zero.

2. The IMD of claim 1, wherein the processor decreases the frequency at which the most recent electrical signal is analyzed when the heart rate parameter falls below a second heart rate parameter threshold.

3. The IMD of claim 1, wherein the heart rate parameter comprises one of a heart rate and a relative change in the heart rate.

4. The IMD of claim 1, wherein the processor is configured to obtain a template electrogram and determine whether one or more characteristics of the most recent electrical signal have significantly changed relative to the template electrical signal.

5. The IMD of claim 4, wherein the processor analyzes one of an ST segment of the electrical signal, a T-wave segment of the electrical signal and a QRS segment of the electrical signal.

6. The IMD of claim 1, wherein the processor is configured to obtain an EGM corresponding with a most recent beat, obtain a template EGM corresponding to a beat during a normal sinus, and periodically analyze the most recent cardiac electrical signal by comparing the EGM corresponding with a most recent beat to the template EGM using a wavelet transform analysis.

7. The IMD of claim 1, wherein the electrical conduction abnormality is associated with at least one of a cardiac ischemia, a cardiac infarction, a branch bundle block, or fascicular block.

8. An implantable medical device comprising:
a sensing module configured to acquire cardiac electrical signals corresponding to cardiac activity of a heart of a patient via at least one sensor; and
a processor configured to obtain the cardiac electrical signals corresponding to cardiac activity of the heart of the patient, periodically analyze, at a first frequency, a most recent cardiac electrical signal of the obtained cardiac electrical signals to monitor for an electrical conduction abnormality of the heart, compute at least a heart rate parameter of the patient and a number of premature ventricular contractions (PVCs) using the acquired cardiac electrical signals, compare the heart rate parameter of the patient to a heart rate parameter threshold, compare the number of PVCs to a PVC threshold, increases the frequency at which the most recent electrical signal is analyzed to a second frequency that is larger than the first frequency when the heart rate parameter has changed by the heart parameter threshold and further increases the frequency at which the most recent electrical signal is analyzed to a third frequency that is larger than the second frequency when the number of detected premature ventricular contractions (PVCs) is greater than the PVC threshold.

9. A method comprising:
obtaining electrical signals corresponding to cardiac activity of a heart of a patient;
periodically analyzing, at a first frequency, a most recent electrical signal of the obtained electrical signals to monitor for an electrical conduction abnormality of the heart;

obtaining at least a heart rate parameter of the patient and a number of premature ventricular contractions (PVCs);

comparing the heart rate parameter of the patient to a heart rate parameter threshold;

comparing the number of PVCs to a PVC threshold; and increasing the frequency at which the most recent electrical signal is analyzed to a second frequency when the heart rate parameter of the patient is greater than the heart rate parameter threshold and the number of PVCs detected is greater than the PVC threshold, wherein the first frequency and the second frequency are greater than zero.

10. The method of claim 9, further comprising decreasing the frequency at which the most recent electrical signal is analyzed when the heart rate parameter falls below a second heart rate parameter threshold.

11. The method of claim 9, wherein analyzing the most recent electrical signal of the heart comprises determining whether one or more characteristics of the most recent electrical signal have significantly changed relative to a template electrical signal.

12. The method of claim 11, wherein analyzing the most recent electrical signal of the heart comprises analyzing one of an ST segment of the electrical signal, a T-wave segment of the electrical signal and a QRS segment of the electrical signal.

13. The method of claim 9, wherein the electrical conduction abnormality is associated with at least one of a cardiac ischemia, a cardiac infarction, a branch bundle block, or a fascicular block.

14. The method of claim 9, further comprising performing one of a therapy delivery, a patient notification, an event log in memory and a transmission of a communication in response to detecting the electrical conduction abnormality.

15. The method of claim 9, wherein periodically analyzing a most recent cardiac electrical signal comprises comparing an EGM corresponding with a most recent beat to a template EGM corresponding to a beat during a normal sinus rhythm using a wavelet transform analysis.

16. An implantable medical device comprising:

obtaining electrical signals corresponding to cardiac activity of a heart of a patient;

periodically analyzing, at a first frequency, a most recent electrical signal of the obtained electrical signals to monitor for an electrical conduction abnormality of the heart;

obtaining at least a heart rate parameter of the patient and a number of premature ventricular contractions (PVCs)

comparing the heart rate parameter of the patient to a heart rate parameter threshold comparing the number of PVCs to a PVC threshold;

increasing the frequency at which the most recent electrical signal is analyzed to a second frequency that is larger than the first frequency when the heart rate parameter has changed by the heart parameter threshold; and further increasing the frequency at which the most recent electrical signal is analyzed to a third frequency that is larger than the second frequency when the number of detected premature ventricular contractions (PVCs) is greater than the PVC threshold.

17. An implantable medical device (IMD) comprising:

means for obtaining electrical signals corresponding to cardiac activity of a heart of a patient;

means for periodically analyzing, a first frequency, a most recent electrical signal of the obtained electrical signals to monitor for an electrical conduction abnormality of the heart;

means for obtaining at least a heart rate parameter of the patient and a number of premature ventricular contractions (PVCs);

means for comparing the heart rate parameter of the patient to a heart rate parameter threshold and the number of PVCs to a PVC threshold; and means for increasing the frequency at which the most recent electrical signal is analyzed to a second frequency when the heart rate parameter of the patient is greater than the heart rate parameter threshold and the number of PVCs detected is greater than the PVC threshold, wherein the first frequency and the second frequency are greater than zero.

18. The device of claim 17, wherein the adjusting means further decreases the frequency at which the most recent electrical signal is analyzed when the heart rate parameter falls below a second heart rate parameter threshold.

* * * * *